US005756846A

United States Patent [19]
Driessen-Hölscher et al.

[11] Patent Number: 5,756,846
[45] Date of Patent: May 26, 1998

[54] PROCESS FOR THE PREPARATION OF PRIMARY OCTADIENYLAMINES

[75] Inventors: Birgit Driessen-Hölscher; Wilhelm Keim; Thomas Prinz, all of Aachen; Hans-Joachim Traenckner, Leverkusen; Jörg-Dietrich Jentsch, Ruhr, all of Germany

[73] Assignee: Bayer Aktiengesellschaft, Leverkusen, Germany

[21] Appl. No.: 740,742

[22] Filed: Nov. 4, 1996

[30] Foreign Application Priority Data

Nov. 13, 1995 [DE] Germany .......................... 195 42 188.4
May 28, 1996 [DE] Germany .......................... 196 21 303.7

[51] Int. Cl.$^6$ .................................................. C07C 209/04
[52] U.S. Cl. ......................................................... 564/485
[58] Field of Search ............................................. 564/485

[56] References Cited

U.S. PATENT DOCUMENTS

| | | |
|---|---|---|
| 4,100,194 | 7/1978 | Hobbs et al. |
| 4,104,471 | 8/1978 | Stone et al. |
| 4,130,590 | 12/1978 | Hobbs et al. |
| 4,186,148 | 1/1980 | Murata et al. |
| 4,260,750 | 4/1981 | Kuntz ............................ 544/178 |
| 4,356,333 | 10/1982 | Yoshimura et al. |
| 4,417,079 | 11/1983 | Yoshimura et al. |
| 5,169,981 | 12/1992 | Packett ............................ 560/225 |

FOREIGN PATENT DOCUMENTS

| | | |
|---|---|---|
| 0436226 | 7/1991 | European Pat. Off. |
| 2693188 | 1/1974 | France. |
| 129779 | 2/1978 | Germany. |
| 2733516 | 2/1978 | Germany. |
| 1553002 | 9/1979 | United Kingdom. |

OTHER PUBLICATIONS

R.N. Fachretdinov, et al., Die katalytische Synthese ungesättigter Amine aus Reaktionen des Butadiens mit Ammoniumsalzen organischer und Mineralsäuren. Neftechimija, Bd. 19, No. 3, pp. 1–11, (1979).

P. Kalck, et al., Use of Water–Soluble Ligands in Homogeneous Catalysis, Advances in Organometallic Chemistry, vol. 34, pp. 219–282, (1992).

T. Mitsuyasu, et al.,Syntheses of Long–chain Amines by Palladium–catalysed Telomerisation of Butadiene. J. Chem. Soc., Chemical Communications, p. 345, (1971).

E. Monflier, et al., Palladium catalyzed telomerization of butadiene with water in a two phase system: drastic effect of the amine structure on the rate and selectivity. Journal of Molecular Catalysis A: Chemical, 97, pp. 29–33, (1995).

G. Peiffer, et al., Synthesis of Water–Soluble Ligands With a Quaternary Ammonium Salt: Use in Biphasic Palladium–Catalyzed Telomerisation of Butadiene and Isoprene. Journal of Molecular Catalysis, 59, pp. 1–9, (1990).

J. Tsuji, et al., Palladium–Catalyzed Telomerization of Butadiene With Ammonia. Journal of Molecular Catalysis, 10, pp. 107–114, (1981).

V. Wolfgang A. Herrmann, et al., Wasserlösliche Liganden, Metallkomplexe und Komplexkatalysatoren: Synergismen aus Homogen–und Heterogenkatalyse, Angew. Chem., 105, pp. 1588–1609, (1993).

A. Durocher, et al., Telomerisation von Olefinen in Zwei–Phasen–Systemen, Erdöl und Kohle, 29, pp. 347–354, (1976).

Neftekhimiya, 19, pp. 468–474, (1979).

Journal of Molecular Catalysis, Bd. 10, 1981, Seiten 107–114, XP000196826, Jiro Tsuji, et al.: "Palladium–catalyzed telomerization of butadiene with ammonia", *das ganze Dokument*.

Database WPI, Section Ch, Week 9331, Derwent Publications Ltd., London, GB; Class A60, AN 93–249126, XP002025480 & SU 1 754 705 A (Univ. Irkut Zhdanov), Aug. 15, 1992, *Zusammenfassung*.

Chemical Abstracts, vol. 74, No. 25, Jun. 21, 1971, Columbus, Ohio, U.S.: abstract No. 140785n, Tsuji, Jiro, et al.: "Syntheses of long–chain amines by palladium–catalyzed telomerization of butadiene", Seite 513, Spalte 1; XP002025479, *Zusammenfassung* & J. Chem. Soc. D., Bd. 7, 1971, Seite 345.

*Primary Examiner*—Brian M. Burn
*Attorney, Agent, or Firm*—Sprung Kramer Schaefer & Briscoe

[57] ABSTRACT

Octa-2,7-dienyl-1-amine and octa-1,7-dienyl-3-amine, from which octyl-1-amine can be prepared, are prepared selectively by telomerizing butadiene and ammonia in a two-phase system, the catalyst being used in an aqueous phase and an organic medium which is immiscible or only slightly miscible with water being employed as the second phase.

10 Claims, No Drawings

PROCESS FOR THE PREPARATION OF PRIMARY OCTADIENYLAMINES

The present invention relates to a process for the preparation of primary octadienylamines from ammonia and 1,3-butadiene.

Octadienylamines can be used, for example, as intermediate products for the preparation of octylamines, which in turn are required, for example, for the preparation of fabric softeners, corrosion inhibitors, flotation auxiliaries and emulsifiers. Octyl-1-amine is preferred for this purpose. Those octadienylamines which can be converted into octyl-1-amine therefore have the greatest importance. These are, in particular, octa-2,7-dienyl-1-amine and octa-1,7-dienyl-3-amine.

It is known that a mixture of octadienylamines can be prepared by telomerization of ammonia with 1,3-butadiene. However, to date significant contents of tertiary amines such as tri-(octa-2,7-dienyl)-amine and di-(octa-1,7-dienyl-3)-(octa-2,7-dienyl-1)-amine have always predominantly been obtained in this telomerization because the basicity of the nitrogen increases with increasing degree of alkylation and therefore, in the present case, secondary amines are more reactive than primary amines and primary amines are more reactive than ammonia.

The octadienylamines mentioned hitherto correspond to the following formulae (I) to (IV) and are also designated by the following Roman numerals stated here in the following text.

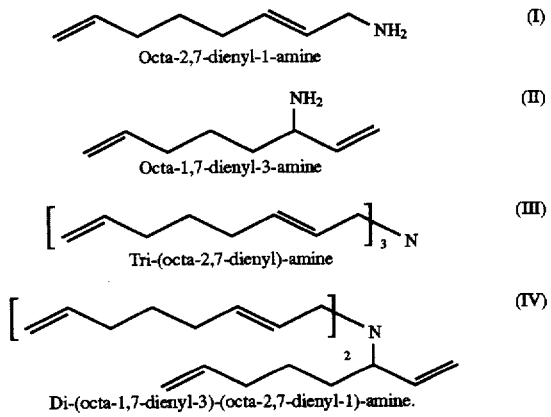

It is known that the telomerization of butadiene with ammonia leads to satisfactory yields only in the presence of water (J. Chem. Soc. Chem. Comm. 1971, 345 and J. Mol. Catal. 1981, 10, 107). Ammonia is therefore employed in the reaction in the form of an aqueous solution. The amines (III) and (IV) are obtained in a total yield of 100%, based on ammonia, with a catalyst system which comprises palladium acetate and triphenylphosphane in a molar ratio of 1:3.5.

The telomerization of 1,3-butadiene with various ammonium salts is furthermore described (Neftekhimiya, 1979, 19, 468). An in situ system of palladium acetylacetonate, triphenylphosphane and triethylaluminum in a ratio of 1:2:3 is used as the catalyst. If ammonium bicarbonate is used as the ammonium salt, a product mixture which comprises at least 5 components, including the amine (II), is obtained. The undesirable tertiary amine (III) and a nitrogen-free dimer of butadiene are formed here to the extent of in each case 25%. If trifluoroacetic acid is added, this telomerization leads to the undesirable tertiary amine (III) with a yield of 25% and a selectivity of 100%. If ammonium tartrate is used instead of ammonium bicarbonate, the product mixture contains only 3 components, of which, however, 59% by weight is nitrogen-free butadiene oligomers. In none of these processes can the linear primary octadienylamine (I) be isolated from the reaction mixture.

It is known from U.S. Pat. Nos. 4 100 194 and 4 130 590 that secondary and tertiary octadienylamines can be prepared from butadiene and ammonia using the catalyst system palladium acetate/diisopropyl(phenyl) phosphonite. Conversion of 98% is observed at a temperature of 70° C. and a reaction time of one hour. If trifluoroacetic acid is added, exclusive formation of the undesirable tertiary amine (III) is also observed here.

If homogeneous reactions catalyzed by transition metal compounds are carried out in two immiscible phases, this enables easy removal of the catalyst from the reaction products (Angew. Chem. 1993, 105, 1588 and Adv. Organomet. Chem. 1992, 34, 219). Telomerization reactions have also already been carried out in two-phase systems, for example the telomerization of phthalic acid with 1,3-butadiene, one phase being formed from dimethyl sulphoxide and the other from isooctane (Erdol und Kohle 1976, 29, 31).

The telomerization of dienes in a two-phase system is known from German Offenlegungsschrift 2 733 516. In this, for the first time water was used as the solvent for the catalyst and the use of sulfonated phosphanes which, after complexing with the transition metal, cause water-solubility thereof, was described. Water, alcohols, phenols, acids, amines, CH-active substances and silanols were employed as nucleophiles. In the case of the reaction of butadiene with amines, only the reaction with diethylamine is given as an example, 1-diethylaminobut-2-ene and 1-N-diethylaminoocta-2,7-diene being formed as products (cf. Examples 25 and 26). Tertiary amines are thus obtained from a secondary amine. Since, as mentioned above, the reactivity of secondary amines toward butadiene is considerably higher than that of ammonia, the process according to the invention cannot be obvious from this German Offenlegungsschrift.

The telomerization of butadiene and water to give octadienols in a two-phase system is known from several patents (cf. U.S. Pat. Nos. 4 356 333 and 4 417 079 and EP Laid-Open Specification 436 226). The reaction here is carried out in an aqueous sulfolane solution, from which the octadienols formed separate out as a second phase. The palladium catalyst is retained in the sulfolane phase by monosulfonated triphenylphosphane (TPPMS).

Water-soluble quaternary ammonium phosphines, as ligands for transition metals, are described in the telomerization of dienes with methanol under two-phase conditions (J. Mol. Catal., 1990, 59, 1).

FR Patent 2 693 188 describes the telomerization of sucrose with butadiene in aqueous solution using a catalyst system of palladium acetate and trisulfonated triphenylphosphane (TPPTS). The conversion with respect to sucrose is 96%. However, various octadienyl ethers of different degrees of alkylation are formed, the diether, triether and tetraether predominating.

The telomerization of butadiene and water in a two-phase system with a trialkylamine as an additive is known from a publication which has recently appeared (J. Mol. Catal. A: Chemical, 1995, 97, 29). The catalyst system comprises a palladium salt and TPPMS or TPPTS. The reaction mixture comprises up to 5 telomerization products (alcohols, olefins and ethers). The reaction is thus non-selective.

Summarizing, it can be said that two-phase telomerizations of butadiene and ammonia have not yet been described, and the processes known from the literature for two-phase telomerizations with butadiene proceed non-selectively.

The present invention is based on the object of carrying out the telomerization of butadiene and ammonia such that the primary octadienylamines (I) and (II) are formed as selectively as possible and the formation of undesirable secondary and tertiary octadienylamines is prevented as far as possible. The amine (I) is practically not obtained and the amine (II) is obtained only with relatively large contents of undesirable products by the telomerization processes known to date.

A process has now been found for selective preparation of octa-2,7-dienyl-1-amine and octa-1,7-dienyl-3-amine, which comprises telomerizing butadiene and ammonia in a two-phase system, the catalyst being used in an aqueous phase and an organic medium which is immiscible or only slightly miscible with water being employed as the second phase.

Possible catalysts are, for example, mixtures of palladium compounds and phosphorus compounds which render these more water-soluble. The palladium can be present in the palladium compounds in the oxidation levels zero, +1 and/or +2. Palladium(II) acetate is particularly suitable. Possible phosphorus compounds are, for example, triphenylphosphanes in the acid and/or salt form. Suitable compounds are, for example, mono-, di- and/or trisulfonated triphenylphosphanes in the acid and/or salt form. Trisulfonated triphenylphosphane in the form of the trisodium salt is particularly preferred. Other phosphorus compounds which render the palladium compounds water-soluble are also possible, for example phosphanes which contain carboxyl or hydroxyl groups.

The palladium catalyst can be employed, for example, in amounts of $7.5 \times 10^{-5}$ to 0.75 mmol of Pd per g of water, and the phosphorus compound which renders the catalyst more water-soluble can be employed, for example, in amounts of 1 to 10 mol per mol of palladium catalyst.

A possible organic medium which is immiscible or only slightly miscible with water is, for example, one of which less than 5 g, in particular less than 3 g, dissolve in 100 g of water at 20° C. Suitable media are, for example, aliphatic and aromatic hydrocarbons and chlorinated aliphatic and aromatic hydrocarbons, such as $C_3$–$C_{30}$-alkanes, benzene, mono-, di- and/or tri-$C_1$–$C_4$-alkylbenzenes, mono- and polychlorinated $C_1$–$C_{12}$-alkanes, mono-, di- and trichlorinated benzenes and mono-, di- and trichlorinated $C_1$–$C_4$-alkylbenzenes. Butadiene can also be used as the organic medium which is immiscible or only slightly miscible with water. In this case, at least 0.5 mol of butadiene is to be employed per mol of ammonia. 0.7 to 100 mol of butadiene per mol of ammonia is preferred in this case. Preferred organic media are methylene chloride, dichloroethane, toluene, pentane and butadiene. Mixtures of various organic media can also be employed.

Ammonia can be employed in any desired form. Aqueous solutions of ammonia, for example 5 to 35% strength by weight aqueous ammonia solutions, or pure ammonia (commercial product) are preferably used.

0.1 to 10,000 ml of water, for example, can be employed per 100 ml of organic medium which is immiscible or only slightly miscible with water, it being possible for the water to be introduced, for example, as such and/or in the form of an aqueous ammonia solution. If a solvent which is immiscible or only slightly miscible with water and differs from butadiene is employed, it can be employed in any desired amounts, 80 to 500 ml of such a solvent per mol of butadiene being preferred.

The process according to the invention can be carried out, for example, at temperatures from 30° to 150° C. under pressures in the range from 1 to 150 bar. It is preferably carried out in a closed vessel under the pressure which is established by itself at the particular reaction temperature.

The reaction time is in general 15 minutes to 4 hours. If appropriate, the most favorable reaction time for the individual case can be determined by routine series of experiments, during which it should be remembered that with a longer reaction time the conversion of butadiene, but also the formation of undesirable secondary and tertiary amines, in general increases. This is particularly pronounced if butadiene and no other organic media is used. It is advantageous to stir the mixture or to shake the reaction vessel during the reaction.

The reaction mixture present after the reaction can be worked up in a simple manner. For example, a procedure can be followed in which the aqueous phase is separated from the organic phase, the aqueous phase is washed with an organic solvent which is immiscible or only slightly miscible with water, preferably with the organic solvent employed in the reaction, the wash liquid is combined with the organic phase which has been separated off, and the resulting telomerization products are separated off therefrom and separated, for example by distillation.

If the reaction has been carried out with butadiene and without an additional solvent, for working up it is in general sufficient first to remove unreacted butadiene or unreacted ammonia, for example by releasing the pressure, and then to separate off the organic phase. The resulting telomerization products can then be separated by distillation of the organic phase.

In a preferred embodiment of the process according to the invention, the catalyst and water are initially introduced into an autoclave at room temperature, aqueous ammonia solution and organic solvent which is immiscible or only slightly miscible with water are added, an appropriate amount of butadiene and, if appropriate, ammonia are then condensed into the autoclave at a low temperature, and, after closing, the autoclave is heated to the reaction temperature. When the reaction has ended, and if appropriate after subsequent stirring, the autoclave is finally brought to room temperature and let down and the reaction mixture present is worked up as described above.

The process according to the invention can be carried out discontinuously or continuously.

The process according to the invention has a number of advantages. Thus, the telomerization product comprises considerably -higher contents of the octadienylamines (I) and (II) than other processes. In the process according to the invention, the selectivity of the formation of (I) and (II) is in general between 70 and virtually 100%. The yields of (I) based on the butadiene employed in the process according to the invention are comparable to or better than those in other processes. If the amounts of butadiene are too low, the content of undesirable secondary amines in the telomerization product increases sharply (cf. Comparison Example 1). If unsuitable organic solvents are used, the selectivity of the formation of (I) and (II) drops to below 35% and only quite low conversions take place (cf. Comparison Example 2).

In particular, the selectivities and yields of (I) and (II) are considerably higher in the process according to the invention than in known processes for the preparation of octadienylamines from ammonia or ammonium compounds and butadiene.

In the process according to the invention, the catalyst is practically exclusively in the aqueous phase after the reaction. It can therefore be separated off easily from the reaction products in the organic phase, and can be recycled in a simple manner.

These advantages are decidedly surprising, since the octadienylamines (I) and (II) to date have not successfully been prepared selectively from butadiene and ammonia or ammonium compounds. In contrast to the process according to the invention, known 2-phase telomerization reactions of butadiene with other nucleophiles, for example with sucrose or water, are unselective.

EXAMPLES

Example 1

A catalyst solution comprising 0.15 mmol of palladium (II) acetate and 0.6 mmol of TPPTS in 5 ml of water was initially introduced into an autoclave flushed with an inert gas, and 20 ml of a 27.13 molar aqueous ammonia solution and 12.5 ml of methylene chloride were added. The autoclave was weighed and then cooled in an ethanol/dry ice bath. 5.8 ml of liquid butadiene were then added and the autoclave was returned to room temperature in the course of one hour. It was weighed again, for precise determination of the weight of butadiene, and then suspended in an oil bath preheated to 100° C. After a reaction time of 1.5 hours, the autoclave was cooled to room temperature with nitrogen and then let down and opened. The contents were transferred to a separating funnel and the phases were separated. The aqueous phase was extracted with 10 ml of methylene chloride. Argon was blown through the combined organic phases to remove residual butadiene. Finally, a sample of the combined organic phases was taken, dried over a molecular sieve and analyzed by gas chromatography.

The results can be seen from Table 1.

Examples 2 to 5

The procedure was as in Example 1,but the reaction temperatures and times were varied. The results can be seen from Table 1.

TABLE 1

| Ex. No. | Reaction temperature (°C.) | Reaction time (hours) | Selectivity of the formation of (I) | (II) | (I) + (II) | Yield of (I), based on butadiene |
|---|---|---|---|---|---|---|
| 1 | 100 | 1.5 | 42% | 28% | 70% | 28% |
| 2 | 80 | 1 | 54% | 39% | 93% | 17% |
| 3 | 80 | 1.5 | 51% | 40% | 91% | 16% |
| 4 | 60 | 1 | 56% | 40% | 96% | 13% |
| 5 | 60 | 2 | 53% | 41% | 94% | 13% |

The selectivity of the formation of secondary amines was 1 to 7%.

Examples 6 to 9 and Comparison Examples 1 to 2

The reaction was carried out at 80° C. and in accordance with Example 1, but with different organic solvents or in the absence of an organic solvent. The results can be seen from Table 2.

TABLE 2

| Ex. No. | Reaction time hours | Solvent | Selectivity of the formation of (I) | (II) | (I) + (II) | sec. Amine | Yield of (I), based on butadiene |
|---|---|---|---|---|---|---|---|
| 6 | 1.5 | $CH_2Cl_2$ | 51% | 40% | 91% | 2% | 16% |
| 7 | 1.5 | $C_2H_4Cl_2$ | 45% | 34% | 79% | 4% | |
| 8 | 1.5 | toluene | 50% | 38% | 88% | 6% | 30% |
| 9 | 1.5 | pentane | 46% | 33% | 79% | 16% | 29% |
| V1 | 1 | — | 34% | 26% | 60% | 30% | |
| V2 | 1.5 | ethyl acetate | 15% | 19% | 34% | n.d. | | n.d. = not determined; V1 and V2 are comparison experiments.

V1 shows that in the absence of an organic solvent, the selectivity of the formation of (I)+(II) decreases significantly and the selectivity of the formation of secondary amines increases greatly. V2 shows that an organic solvent which is not of sufficiently low miscibility with water is used, the selectivity of the formation of (I)+(II) and the yield of (I) decrease very greatly.

Examples 10 to 12

The reaction was carried out at 80° C. in accordance with Example 1, but with different catalyst concentrations and different ratios of palladium catalyst butadiene. The results can be seen from Table 3.

TABLE 3

| Ex. No. | Concentration of the catalyst (mol/l) | Molar ratio of Pd:Butadiene | Selectivity of the formation of (I) | (II) | (I) + (II) | Yield of (I), based on butadiene |
|---|---|---|---|---|---|---|
| 10 | $1.2 \times 10^{-2}$ | 1:260 | 45% | 43% | 88% | 7% |
| 11 | $6 \times 10^{-3}$ | 1:520 | 49% | 41% | 90% | 17% |
| 12 | $3 \times 10^{-3}$ | 1:947 | 51% | 41% | 92% | 13% |

Example 13

1.5 mol of palladium(II) acetate were first initially introduced into a Schlenk tube and dissolved in 20 ml of 25% strength by weight aqueous ammonia solution. 4.5 mmol of TPPTS were then added.

200 ml of water were initially introduced into a 900 ml stirred vessel and the catalyst solution prepared in the Schlenk tube was added to this. 45 g of ammonia and then 120 g of butadiene were metered in, while stirring. The autoclave was heated to 60° C., while stirring vigorously, and in each case a sample was taken after 45 and 75 minutes. 1 ml of toluene was added to each of the samples taken (about 3 ml). After the phases had been separated, the organic phase was dried over a molecular sieve and analyzed by gas chromatography.

The results can be seen from Table 4.

Example 14

The procedure was as in Example 13, but the reaction mixture was heated to 80° C. and a sample was taken after 30 minutes and analyzed. The results can be seen from Table 4.

TABLE 4

| Exam-ple No. | Reaktion temperature | time | Selectivity of the formation of (I) + (II) | secondary amine | tertiary amine | Conversion of butadiene |
|---|---|---|---|---|---|---|
| 13 | 60° C. | 45 min | 94% | 5% | — | 6% |
| 13 | 60° C. | 75 min | 92% | 7% | — | 20.5% |
| 14 | 80° C. | 30 min | 88% | 10% | — | 39% |

We claim:

1. A process for the selective preparation of octa-2,7-dienyl-1-amine and octa-1,7-dienyl-3-amine by telomerizing butadiene and ammonia in a two-phase system comprising an organic phase and an aqueous phase, in the presence of a catalyst, wherein the organic phase is comprised of an organic medium which is immiscible or only slightly miscible with water, and the catalyst is used in the aqueous phase.

2. The process of claim 1, wherein said catalyst is a palladium compound mixed with a phosphorous compound which increases the water solubility of said palladium compound.

3. The process as claimed in claim 1, wherein $7.5 \times 10^{-5}$ to 0.75 mmol of palladium (per g of water) and 1 to 10 mol of a compound which renders the palladium more water-soluble (per mol of palladium) are employed as the catalyst.

4. The process as claimed in claim 1, wherein the organic medium employed is one of which less than 3 g dissolve in 100 g of water at 20° C.

5. The process as claimed in claim 1, wherein one or more of $C_3$–$C_{30}$-alkanes, benzene, mono-, di- and tri-$C_1$–$C_4$-alkylbenzenes, mono- and polychlorinated $C_1$–$C_{12}$-alkanes, mono-, di- and trichlorinated benzenes and mono-, di- and trichlorinated $C_1$–$C_4$-alkylbenzenes and butadiene are employed as the organic medium.

6. The process as claimed in claim 1, wherein ammonia is employed as a 5 to 35% strength by weight aqueous solution.

7. The process as claimed in claim 1, wherein 0.1 to 10,000 ml of water per 100 ml of organic medium and 80 to 500 ml of organic solvent per mol of butadiene are employed.

8. The process as claimed in claim 1, wherein at least 0.5 mol of butadiene is employed per mol of ammonia.

9. The process as claimed in claim 1, which is carried out at 30° to 150° C. under 1 to 150 bar.

10. The process as claimed in claim 1, wherein the reaction mixture is worked up by separating the aqueous phase from the organic phase, washing the aqueous phase with an organic solvent which is immiscible or only slightly miscible with water, combining the wash liquid with the organic phase which has been separated off and separating off the resulting telomerization products therefrom and separating them.

* * * * *